(12) United States Patent
Zhou et al.

(10) Patent No.: US 10,905,433 B2
(45) Date of Patent: Feb. 2, 2021

(54) AURICLE CLAMP AND DELIVERY DEVICE THEREOF

(71) Applicant: BEIJING MED ZENITH MEDICAL SCIENTIFIC CO., LTD., Beijing (CN)

(72) Inventors: Qingliang Zhou, Beijing (CN); Jinshan Li, Beijing (CN); Danian Ke, Beijing (CN); Jian Meng, Beijing (CN)

(73) Assignee: Beijing Med Zenith Medical Scientific Co., Ltd.

( * ) Notice: Subject to any disclaimer, the term of this patent is extended or adjusted under 35 U.S.C. 154(b) by 177 days.

(21) Appl. No.: 15/744,065

(22) PCT Filed: Jun. 6, 2016

(86) PCT No.: PCT/CN2016/084948
§ 371 (c)(1),
(2) Date: Jan. 12, 2018

(87) PCT Pub. No.: WO2017/024879
PCT Pub. Date: Feb. 16, 2017

(65) Prior Publication Data
US 2018/0199945 A1 Jul. 19, 2018

(30) Foreign Application Priority Data

Aug. 11, 2015 (CN) .......................... 2015 1 0505137

(51) Int. Cl.
*A61B 17/122* (2006.01)
*A61B 17/00* (2006.01)
*A61B 17/128* (2006.01)

(52) U.S. Cl.
CPC ...... *A61B 17/1227* (2013.01); *A61B 17/0057* (2013.01); *A61B 17/122* (2013.01); *A61B 17/1285* (2013.01)

(58) Field of Classification Search
CPC . A61B 17/122; A61B 17/1227; A61B 17/128; A61B 2017/00584;
(Continued)

(56) References Cited

U.S. PATENT DOCUMENTS 5,275,614 A * 1/1994 Haber ................ A61B 17/0469
606/139
8,647,350 B2 2/2014 Mohan
(Continued)

FOREIGN PATENT DOCUMENTS

AU 2007202365 1/2008
CN 101467908 A 7/2009
(Continued)

OTHER PUBLICATIONS

European Search Report dated Mar. 11, 2019 for the corresponding European patent application.
(Continued)

*Primary Examiner* — Thomas McEvoy
(74) *Attorney, Agent, or Firm* — Van Pelt, Yi & James LLP

(57) ABSTRACT

Disclosed are an auricle clamp (101) and a delivery device thereof. The auricle clamp (101) includes two parallel clamp arms (202, 302); and two springs (201, 301) located at two ends of the parallel clamp arms (202, 302) respectively and are used for connecting the two ends of the two clamp arms (202, 302) to form a closed-loop structure and providing a clamping force enabling the two clamp arms (202, 203) to be located close to each other; and at least one of the two clamp arms (202, 302) is divided into a first segment and a second segment, and the first segment and the second segment are pivotally connected or connected via a flexible material. The delivery device includes a handle; a coupler (105) capable of rotating relative to the handle; an outer tube
(Continued)

(104) connected with the coupler (105), wherein the outer tube (104) rotates about a centre axis of the outer tube (104) with the rotation of the coupler (105); a liner tube (103) capable of moving within the outer tube (104) along the centre axis of the outer tube (104); a trigger (106), which is connected to an end of the liner tube (103) close to the handle so as to push the liner tube (103) to move within the outer tube (104); and upper teeth and lower teeth, which are connected to the liner tube (103) respectively so as to pivot relative to the outer tube (104) with the movement of the liner tube (103) within the outer tube (104) to facilitate the scissor-type opening and closing of the upper teeth and lower teeth.

9 Claims, 5 Drawing Sheets

(58) Field of Classification Search
CPC ......... A61B 17/0206; A61B 2017/2929; A61F 5/0063; A61F 5/0083; A61F 5/0086; A45D 8/20; A45D 8/22; A45D 8/24; A45D 8/26; A45D 8/28; A45D 8/32
See application file for complete search history.

(56) References Cited

U.S. PATENT DOCUMENTS

| | | | |
|---|---|---|---|
| 9,017,349 B2 | 4/2015 | Privitera et al. | |
| 9,474,516 B2 | 10/2016 | Clark | |
| 9,486,225 B2 | 11/2016 | Michler et al. | |
| 2004/0044363 A1 | 3/2004 | Fowler | |
| 2006/0004388 A1* | 1/2006 | Whayne | A61B 17/10 606/151 |
| 2008/0208324 A1 | 8/2008 | Glithero et al. | |
| 2009/0012545 A1* | 1/2009 | Williamson, IV | A61B 17/083 606/157 |
| 2010/0204716 A1 | 8/2010 | Stewart et al. | |
| 2011/0046437 A1 | 2/2011 | Kassab et al. | |
| 2012/0059400 A1 | 3/2012 | Williamson, IV | |
| 2012/0175398 A1* | 7/2012 | Sandborn | A61B 17/072 227/175.1 |
| 2015/0073439 A1 | 3/2015 | Dannaher | |
| 2015/0190137 A1 | 7/2015 | Salas | |
| 2015/0201946 A1 | 7/2015 | Shepard | |

FOREIGN PATENT DOCUMENTS

| | | |
|---|---|---|
| CN | 203074795 U | 7/2013 |
| CN | 104107072 | 10/2014 |
| CN | 102573665 B | 1/2016 |
| CN | 105193471 B | 10/2017 |
| EP | 625335 | 11/1994 |
| JP | H07275253 | 10/1995 |
| KR | 1020070031820 A | 3/2007 |
| KR | 1020150070866 A | 6/2015 |
| RU | 2261057 | 9/2005 |
| WO | 2007019268 A2 | 2/2007 |
| WO | 2007102151 A2 | 9/2007 |
| WO | 2015095333 A1 | 6/2015 |

OTHER PUBLICATIONS

KIPO office action dated May 21, 2019 for the corresponding Korean patent application.

* cited by examiner

AURICLE CLAMP AND DELIVERY DEVICE THEREOF

FIELD OF THE INVENTION

The present invention relates to the field of medical apparatus and instruments, and in particular to an auricle clamp and a delivery device thereof.

BACKGROUND OF THE INVENTION

Atrial fibrillation is one of the most common clinical arrhythmias, and a large number of patients suffer from it. At present, there are about 8 million atrial fibrillation patients in China and the number is increasing year by year. In patients with atrial fibrillation, 0.4%-1% of them suffer from cerebral apoplexy every year, that is to say, of the 8 million patients, 32,000 to 80,000 people may have cerebral arterial thrombosis due to the atrial fibrillation each year. Cerebral apoplexy is the greatest harm from atrial fibrillation, and studies show that 15-20% of cerebral arterial thrombosis is caused by the atrial fibrillation, and about one in 6 cerebral apoplexy patients is an atrial fibrillation patient. The incidence of cerebral apoplexy in patients with nonvalvular atrial fibrillation is 5.6 times that in normal people and the incidence of valvular atrial fibrillation in cerebral apoplexy is 17.6 times that in normal people; and furthermore, cerebral apoplexy caused by the atrial fibrillation has more serious consequences, with the mortality and disability rate reaching 70%. For patients with valvular atrial fibrillation, 57% of atrial thrombi originate from the left auricle, and for patients with nonvalvular atrial fibrillation, 90% of left atrial thrombi originate from the left auricle. Even after the restoration of sinus rhythm, the left auricle has stunned contractions, and there is still the possibility of thrombosis.

Currently there are three main ways to prevent the cerebral arterial thrombosis caused by atrial fibrillation clinically. One method is to take anticoagulant drugs such as warfarin, but the use of warfarin has a risk of bleeding, requires frequent monitoring, and have many contraindications, and thus its clinical application is difficult; and in addition, warfarin may lead to osteoporosis and soft tissue necrosis. The second method is to directly remove or ligate the auricle during the cardiac surgery, the main disadvantage of this method is that the complete closure rate of the left auricle is relatively low, and previous studies show that the highest success rate of completely resecting the left auricle is about 80%. The third method is to close the left auricle using an instrument by means of percutaneous intervention with an intracardiac left atrial appendage closure product, such as PLAATO (Percutaneous Left Atrial Appendage Transcatheter Occlusion), WATCHMAN, ACP (Amplatzer Cardiac Plug) and so on. Although there are many left auricle occlusion products for intracardiac intervention, the operation is complex, the risk is higher, and the safety and effectiveness are to be verified. Researches by PROTECK-AF show a trend that the safety and the effectiveness of the interventional left auricle occlusion treatment are better than those of the warfarin; serious adverse events occur within a month after the left auricle occlusion treatment, and longer follow-up is required so as to determine the long-term safety and efficacy of the occlusion treatment.

SUMMARY OF THE INVENTION

(1) Technical Problem to be Solved

The objective of the present invention is to design an auricle clamp and a delivery device thereof. The auricle clamp is placed in the root of the left auricle from the outside of the heart in thoracotomy or minimally invasive surgery to permanently close the left auricle.

(2) Technical Solution

The present invention provides an auricle clamp, including two parallel clamp arms; and two springs located at two ends of the parallel clamp arms respectively, for connecting the two ends of the two clamp arms to form a closed-loop structure and providing a clamping force enabling the two clamp arms to be located close to each other; wherein at least one of the two clamp arms is divided into a first segment and a second segment, and the first segment and the second segment are pivotally connected or connected via a flexible material. Preferably, each one of the two clamp arms is divided into the first segment and the second segment, and the first segment and the second segment are pivotally connected.

Preferably, the springs are U-shaped springs.

Preferably, the first segment and the second segment are straight rod-shaped tubes.

Preferably, the springs and the straight rod-shaped tubes are made of at least one of stainless steel, a cobalt-based alloy, a platinum-iridium alloy, a nickel-titanium alloy and a magnesium-based alloy.

Preferably, after the two ends of the U-shaped spring are respectively inserted into the straight rod-shaped tubes, the U-shaped spring and the straight rod-shaped tubes can be combined together by a connecting point in an extrusion deformation, welding, adhesion or threaded connection manner.

Preferably, the flexible material is a nickel-titanium lining wire, and the two straight rod-shaped tubes of each of the clamp arms are connected in such a manner that the nickel-titanium lining wire is inserted into the two straight rod-shaped tubes, and the nickel-titanium lining wire and the two straight rod-shaped tubes are fixed together by extrusion deformation.

Preferably, the outermost layers of the clamp arms and/or the springs are wrapped with a polyester vascular prosthesis or polyester braided fabric.

The present invention further provides a delivery device for conveying the auricle clamp to the root of the auricle, the delivery device including a handle; a coupler connected with the handle and capable of rotating relative to the handle; an outer tube connected with the coupler, wherein the outer tube rotates about a centre axis of the outer tube with the rotation of the coupler; a liner tube capable of moving within the outer tube along the centre axis of the outer tube; a trigger connected with the handle and capable of moving relative to the handle, wherein the trigger is connected to an end of the liner tube close to the handle so as to push the liner tube to move within the outer tube; and upper teeth and lower teeth pivotally connected to an end of the outer tube away from the handle, wherein the upper teeth and the lower teeth are connected to the liner tube respectively so as to pivot relative to the outer tube with the movement of the liner tube within the outer tube to facilitate the scissor-type opening and closing of the upper teeth and lower teeth.

Preferably, the upper teeth and the lower teeth are provided with buckling devices capable of detachably fixing the auricle clamp.

Preferably, a chute is formed in the outer tube, so that the liner tube can move along the chute.

Preferably, the delivery device is provided with a self locking device for locking the positions of the outer tube and/or the liner tube. The self locking device can be a fixing pin, a chute pin or the like.

Preferably, the delivery device further includes an unlocking button for release from a lock state of the self locking device.

Preferably, the auricle clamp is fixed in the upper teeth and the lower teeth of the delivery device in a bundling or mutual clamping manner.

Preferably, the auricle clamp provides a sustained and stable closing force and is implanted in the root of the auricle to effectively block the blood flow of the left atrium and the left auricle.

Preferably, the delivery device conveys the auricle clamp to a target position, controls the opening and closing state of the auricle clamp and can effectively release the auricle clamp.

Preferably, the polyester vascular prosthesis or the polyester braided fabric wrapping the outermost layers of the clamp arms and the springs can form an outer sleeve, and has good biocompatibility, thereby facilitating tissue climbing; and its texture is soft, thereby reducing the instrument's pressure on tissues and reducing damage to the tissues.

Preferably, the outer sleeve can be composed of a high molecular material, such as PET, PTFE or the like.

Preferably, the delivery device can control the opening and closing of the auricle clamp and can achieve an in vivo rotation function of the auricle clamp.

Preferably, the auricle clamp is installed on the delivery device in a bundling or mutual clamping manner, and free detachment of the auricle clamp can be achieved.

Preferably, the auricle clamp is pre-installed, or assembled prior to use, onto the delivery device.

Preferably, the delivery device can keep an open state of the product through the self locking device.

(3) Beneficial Effects

The auricle clamp and the delivery device provided by the present invention have the following advantages:

1. the sizes of the parts of the auricle clamp and the delivery device entering the human body are small, so that the auricle clamp and the delivery device can be applied to establishing an entrance using a puncture outfit (Tocar) to perform minimally invasive surgery;

2. the structure of the springs of the auricle clamp can provide a stable closing force;

3. the polyester vascular prosthesis is used on the outer layer of the auricle clamp, thereby facilitating tissue growth and reducing the drop risk of the product; and 4. the delivery device can rotate around the axis, thereby facilitating the adjustment of the product in the surgery.

REFERENCE SIGNS IN THE DRAWINGS

Figure 1A:
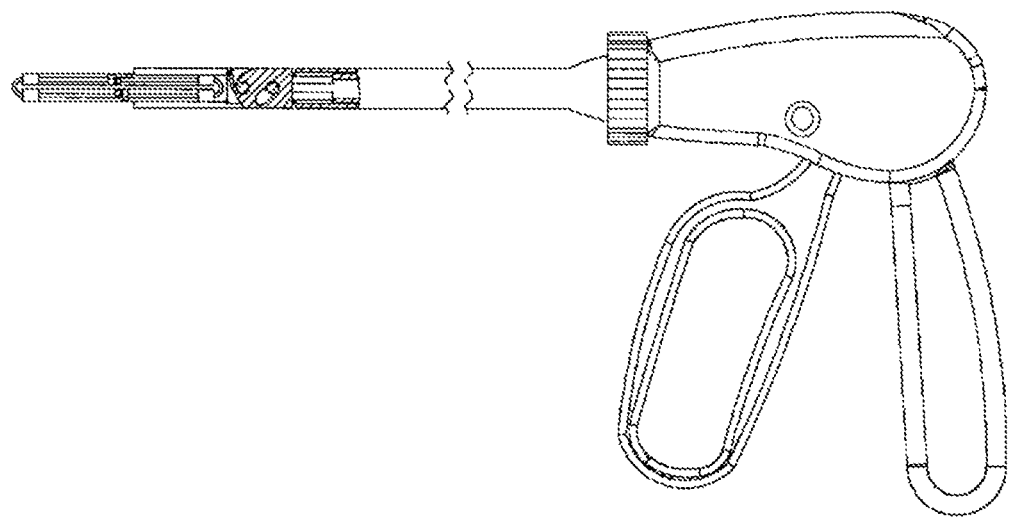
FIG. 1A to FIG. 1C are planar schematic diagrams of an auricle clamp and a delivery device of the present invention.

101: auricle clamp; 102: moving head; 103: liner tube; 104: outer tube; 105: coupler; 106: trigger; 107: unlocking button; 201: U-shaped spring; 202: clamp arm; 203: nickel-titanium wire; 301: spring; 302: clamp arm; 303: lining wire.

DETAILED DESCRIPTION OF THE EMBODIMENTS

The specific embodiments of the present invention will be described in further detail below in conjunction with the drawings and embodiments. The following examples are used for illustrating the present invention, rather than limiting the scope of the present invention.

An auricle clamp of the present invention includes: two parallel clamp arms; and two springs located at two ends of the parallel clamp arms respectively, for connecting the two ends of the two clamp arms to form a closed-loop structure and providing a clamping force enabling the two clamp arms to be located close to each other. At least one of the two clamp arms is divided into a first segment and a second segment, it is the best that each one of the two clamp arms is divided into the first segment and the second segment, the first segment and the second segment are pivotally connected or connected via a flexible material, for example, a flexible wire is inserted into the first segment and the second segment, so that the first segment and the second segment can flexibly rotate relative to each other.

The springs can be U-shaped springs, spiral springs, coil springs or any other suitable form.

The first segment and the second segment can be straight rod-shaped tubes.

The springs and the straight rod-shaped tubes can be made of at least one of stainless steel, a cobalt-based alloy, a platinum-iridium alloy, a nickel-titanium alloy and a magnesium-based alloy.

After the two ends of the U-shaped spring are respectively inserted into the straight rod-shaped tubes, the U-shaped spring and the straight rod-shaped tubes can be combined together by a connecting point in an extrusion deformation, welding, adhesion or threaded connection manner.

The flexible material is a nickel-titanium lining wire, the two straight rod-shaped tubes of the clamp arms are connected in such a manner that the nickel-titanium lining wire is inserted into the two straight rod-shaped tubes, and the nickel-titanium lining wire and the two straight rod-shaped tubes are fixed together by extrusion deformation.

The outermost layers of the clamp arms and/or the springs are wrapped with a polyester vascular prosthesis or polyester braided fabric.

A delivery device for conveying the auricle clamp to the root of the auricle of the present invention can include: a handle; a coupler connected with the handle and capable of rotating relative to the handle; an outer tube connected with the coupler, wherein the outer tube rotates about a centre axis of the outer tube with the rotation of the coupler; a liner tube capable of moving within the outer tube along the centre axis of the outer tube; a trigger connected with the handle and capable of moving relative to the handle, wherein the trigger is connected to an end of the liner tube close to the handle so as to push the liner tube to move within the outer tube; and upper teeth and lower teeth pivotally connected to an end of the outer tube away from the handle, wherein the upper teeth and the lower teeth are connected to the liner tube respectively so as to pivot relative to the outer tube with the movement of the liner tube within the outer tube to facilitate the scissor-type opening and closing of the upper teeth and lower teeth.

The auricle clamp is fixed in the upper teeth and the lower teeth in a bundling or mutual clamping manner. Specifically, the upper teeth and the lower teeth are provided with buckling devices capable of detachably fixing the auricle clamp, or the auricle clamp is bundled on the upper teeth and the lower teeth.

A chute can be formed in the outer tube, so that the liner tube can move along the chute.

The delivery device can be provided with a self locking device for locking the positions of the outer tube and/or the liner tube. The self locking device can be a fixing pin, a chute pin or the like. In this case, the delivery device further includes an unlocking button for release from a lock state of the self locking device.

The auricle clamp provides a sustained and stable closing force and is implanted in the root of the auricle to effectively block the blood flow of the left atrium and the left auricle.

The delivery device conveys the auricle clamp to a target position, controls the opening and closing state of the auricle clamp and can effectively release the auricle clamp.

The polyester vascular prosthesis or the polyester braided fabric wrapping the outermost layers of the clamp arms and the springs can form an outer sleeve, and has good biocompatibility, thereby facilitating tissue climbing; and its texture is soft, thereby reducing the instrument's pressure on tissues and reducing damage to the tissues.

The outer sleeve can be composed of a high molecular material, such as PET, PTFE or the like.

The delivery device can control the opening and closing of the auricle clamp and can achieve an in vivo rotation function of the auricle clamp.

The auricle clamp is installed on the delivery device in a bundling or mutual clamping manner, and free detachment of the auricle clamp can be achieved. The auricle clamp is pre-installed, or assembled prior to use, onto the delivery device. The delivery device can keep an open state of the product through the self locking device.

Figure 1B:
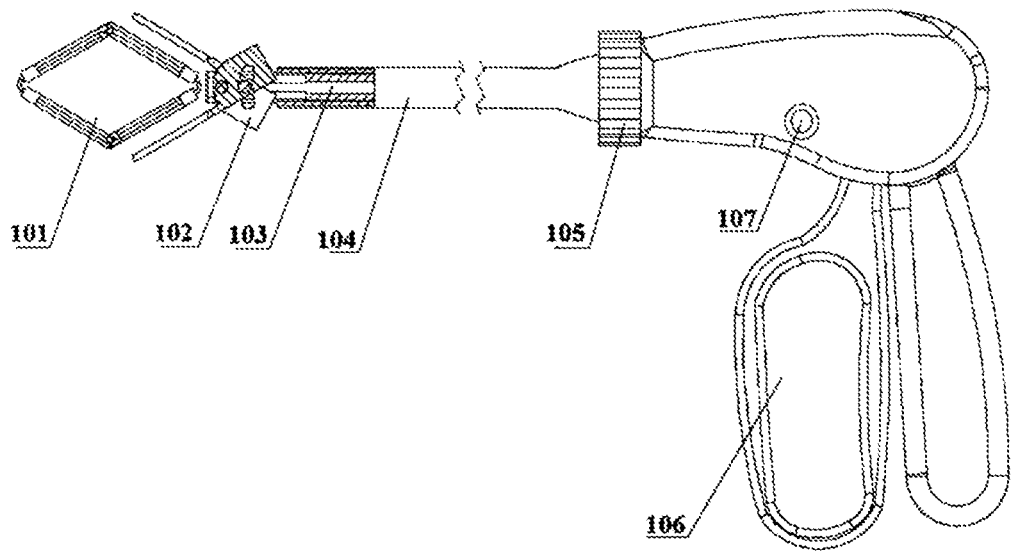
Figure 1C:
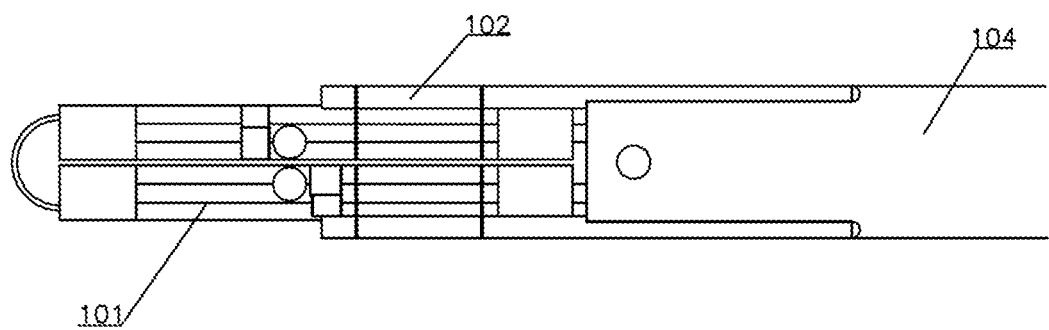

FIG. 1A to FIG. 1C show schematic diagrams of the auricle clamp and the delivery device of the present invention. FIG. 1A shows an initial state, namely a clamped state, of the product; and as shown in FIG. 1B, the auricle clamp and the delivery device include an auricle clamp 101 and a delivery device. Description of the specific structure of the auricle clamp 101 is as follows.

The delivery device includes: a handle; a coupler 105 connected with the handle and capable of rotating relative to the handle; an outer tube 104 connected with the coupler 105, wherein the outer tube 104 rotates about a centre axis of the outer tube 104 with the rotation of the coupler; a liner tube 103 capable of moving within the outer tube along the centre axis of the outer tube 104; a trigger 106 connected with the handle and capable of moving relative to the handle, wherein the trigger 106 is connected to an end of the liner tube 103 close to the handle so as to push the liner tube 103 to move within the outer tube 104; and upper teeth and lower teeth pivotally connected to an end of the outer tube 104 away from the handle, wherein the upper teeth and the lower teeth are connected to the liner tube 103 respectively so as to pivot relative to the outer tube 104 with the movement of the liner tube 103 within the outer tube 104 to facilitate the scissor-type opening and closing of the upper teeth and lower teeth. In the present embodiment, the upper teeth and the lower teeth are connected to the outer tube through a moving head 102 on a distal end of the outer tube 104. For the specific structures of the parts of the delivery device, reference can be made to similar delivery devices in the prior art, for example, ultrasound knives, abdominal forceps and other tools used for surgical operations.

The auricle clamp 101 can be fixed in the upper teeth and the lower teeth in the bundling or mutual clamping manner. Specifically, the upper teeth and the lower teeth are provided with buckling devices capable of detachably fixing the auricle clamp, or the auricle clamp is bundled on the upper teeth and the lower teeth. For the specific structure, reference can be made to similar structures in the prior art, and this thus will not be repeated here.

A chute can be formed in the outer tube 104, so that the liner tube can move along the chute.

The delivery device can be provided with a self locking device for locking the positions of the outer tube and/or the liner tube. The self locking device can be a fixing pin, a chute pin or the like (not shown, for the specific structure, reference can be made to similar structures in the prior art, and this will not be repeated here). In this case, the delivery device further includes an unlocking button 107 for release from a lock state of the self locking device.

The delivery device of the present invention can operate as follows. As shown in FIG. 1C, the auricle clamp 101 is fixed in the upper teeth and the lower teeth of the moving head 102 in the bundling (or mutual clamping configuration) manner; an operator uses an intuitive method such as endoscope or other method to transport the delivery device with the auricle clamp 101 to a place close to the auricle position to be clamped, and pulls the trigger 106 so that the upper teeth and the lower teeth open in a scissor type so as to expand the auricle clamp 101 into a quadrilateral shape as shown in FIG. 1B, and the open state is locked by the self locking device. The position of the auricle clamp can be adjusted by rotating the coupler 105 to thereby rotate the auricle clamp. After the position is finally determined, the unlocking button 107 is actuated for release from the lock state of the self locking device, and the device returns to the initial state, as shown in FIG. 1A. After the operation is completed, the operator cuts it at the bundling point or enables release from the buckled state, and the auricle clamp is detached immediately from the delivery device.

As mentioned above, the auricle clamp and the delivery device of the present invention can establish an entrance using a puncture outfit to cooperate with a laparoscope to perform minimally invasive surgery. Of course, other use methods can also available. For example, the auricle clamp and the delivery device of the present invention are used during thoracotomy.

The auricle clamp in the present invention provides a stable closing force by means of the springs, the clamp arms permanently close the left auricle from the outside of the heart, and some specific examples of the auricle clamp of the present invention are given below.

Figure 2A:
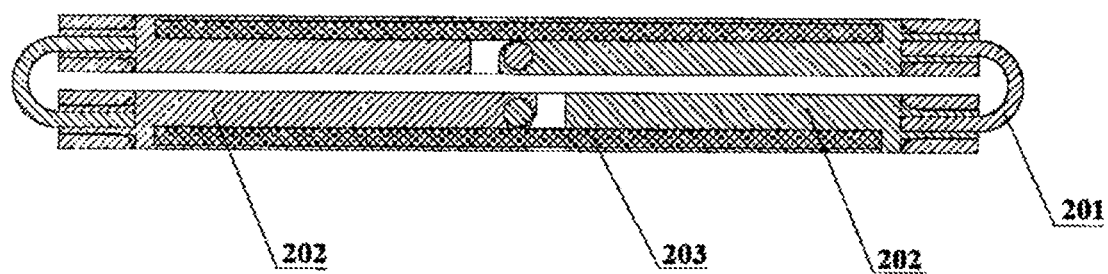
FIG. 2A to FIG. 2C are schematic diagrams of a first embodiment of the auricle clamp of the present invention.

The specific structure of the first embodiment:

As shown in FIG. 2A, which illustrate an initial state of the auricle clamp, the auricle clamp 101 includes two U-shaped springs 201 and two parallel clamp arms 202. Each clamp arm 202 is divided into a first segment and a second segment, the first segment and the second segment are connected in a hinged manner, the two springs 201 are located at two ends of the parallel clamp arms respectively and are used for connecting the two ends of the two clamp arms to form a closed-loop structure and providing a clamping force enabling the two clamp arms to be located close to each other. The two U-shaped springs 201 are respectively inserted into left and right clamp arms and are fixed in a welding or force fit manner.

Figure 2B:
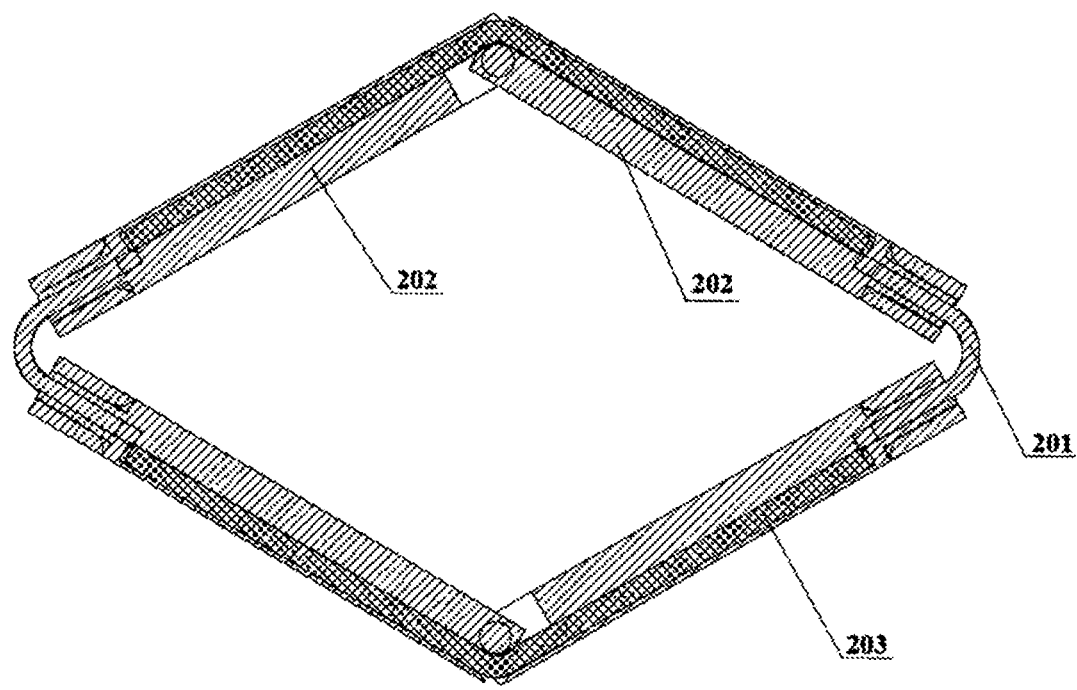
Figure 2C:
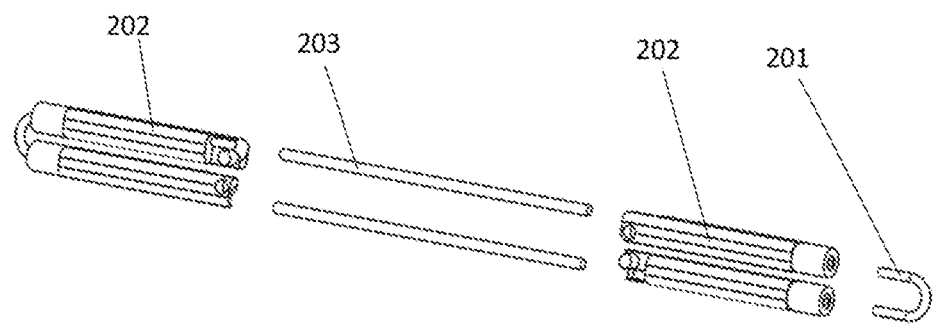

In addition, a nickel-titanium wire 203 can be provided in the hole of the clamp arm. The auricle clamp is placed at the root of the auricle by the delivery device, and after the auricle is clamped, the U-shaped springs on the two ends of the auricle clamp deform due to the thickness of the auricle so as to provide the clamping force for the clamp arms to close the auricle, and meanwhile the nickel-titanium wire is beneficial for ensuring the straightness of the hinged sites of the two clamp arms; FIG. 2B shows the auricle clamp is pulled into a parallelogram; and FIG. 2C is an exploded structure diagram of the auricle clamp.

Figure 3:
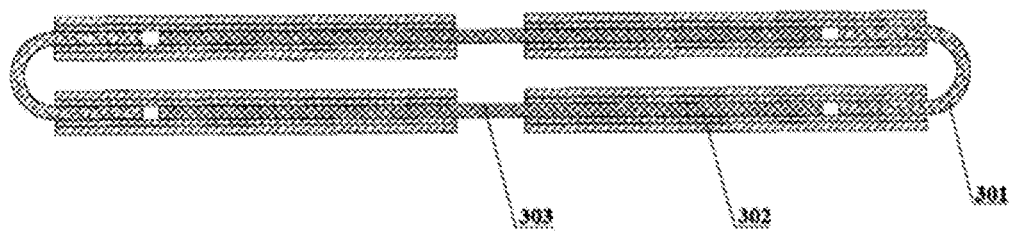
FIG. 3 is a schematic diagram of a second embodiment of the auricle clamp of the present invention.

The specific structure of the second embodiment:

As shown in FIG. 3, which illustrate an initial state of the auricle clamp, the auricle clamp 101 includes two parallel clamp arms 302; and two springs 301 located at two ends of the parallel clamp arms respectively, for connecting the two ends of the two clamp arms to form a closed-loop structure and providing a clamping force enabling the two clamp arms to be located close to each other. Each one of the two clamp arms 302 is divided into a first segment and a second segment, being different from the first embodiment in that the first segment and the second segment are not connected in the hinged manner, but are connected via a flexible material, such as a nickel-titanium lining wire 303; the U-shaped springs 301 and the clamp arms 302 are fixed in a welding or force fit manner, and the nickel-titanium lining wire 303 and the clamp arms 302 tubes are fixed in the welding or force fit manner; and the lining wire 303 is bent when the auricle clamp 101 is opened, and the auricle clamp becomes a quadrangle after being opened, and after the delivery device places the auricle clamp at the root of the auricle, the springs deform due to the thickness of the auricle to provide a clamping force for the clamp arms so as to close the left auricle, and meanwhile the nickel-titanium lining wire 303 guarantees the straightness of the two clamp arms.

The present invention has the following advantages:

1. the sizes of the parts of the auricle clamp and the delivery device entering the human body are small, so that the auricle clamp and the delivery device can be applied to establishing an entrance using a puncture outfit (Tocar) to perform minimally invasive surgery;

2. the structure of the springs of the auricle clamp can provide a stable closing force;

3. the polyester vascular prosthesis is used on the outer layer of the auricle clamp, thereby facilitating tissue growth and reducing the drop risk of the product; and 4. the delivery device can rotate around the axis, thereby facilitating the adjustment of the product in the surgery.

Described above are only preferred embodiments of the present invention, which are not intended to limit the present invention, and any modifications, equivalent replacements, improvements and the like made within the spirit and principle of the present invention shall be encompassed within the protection scope of the present invention.

INDUSTRIAL APPLICABILITY

The present invention provides an auricle clamp, including two parallel clamp arms; and two springs located at two ends of the parallel clamp arms respectively, for connecting the two ends of the two clamp arms to form a closed-loop structure and providing a clamping force enabling the two clamp arms to be located close to each other, wherein at least one of the two clamp arms is divided into a first segment and a second segment, and the first segment and the second segment are pivotally connected or connected via a flexible material. The present invention further provides a delivery device for conveying the auricle clamp to the root of the auricle, the delivery device including a handle; a coupler connected with the handle and capable of rotating relative to the handle; an outer tube connected with the coupler, wherein the outer tube rotates about a centre axis of the outer tube with the rotation of the coupler; a liner tube capable of moving within the outer tube along the centre axis of the outer tube; a trigger connected with the handle and capable of moving relative to the handle, wherein the trigger is connected to an end of the liner tube close to the handle so as to push the liner tube to move within the outer tube; and upper teeth and lower teeth pivotally connected to an end of the outer tube away from the handle, wherein the upper teeth and the lower teeth are connected to the liner tube respectively so as to pivot relative to the outer tube with the movement of the liner tube within the outer tube to facilitate the scissor-type opening and closing of the upper teeth and lower teeth. The auricle clamp of the present invention is fixed in the upper teeth and the lower teeth of the moving head in the bundling or (mutual clamping configuration) manner; the operator uses an intuitive method such as endoscope or other method to transport the delivery device with the auricle clamp to a position close to the auricle to be clamped, and pulls the trigger so that the upper teeth and the lower teeth open in a scissor type so as to expand the auricle clamp into a quadrilateral shape, and the open state is locked by the self locking device. The position of the auricle clamp can be adjusted by rotating the coupler to thereby rotate the auricle clamp. After the position is finally determined, the unlocking button is actuated for release from the lock state of the self locking device, and the device returns to the initial state, and after the operation is completed, the operator cuts it at the bundling point or enables a release from the buckled state, and the auricle clamp is detached immediately from the delivery device. Therefore the practicability is high.

The invention claimed is:

1. An auricle clamp sized for heart surgery, comprising:
two clamp arms; and
two springs located at two ends of the clamp arms respectively and are used for connecting the two ends of the two clamp arms to form a closed-loop structure and providing a clamping force enabling the two clamp arms to be located close to each other;
wherein each of the two clamp arms comprises:
a first rod-shaped tube segment and a second rod-shaped tube segment joined at a respective hinge site; and
a flexible lining wire inserted into the first rod-shaped tube segment and the second rod-shaped tube segment such that the first rod-shaped tube segment and the second rod-shaped tube segment are pivotally connected; and wherein:
in a first state, the two clamp arms are substantially parallel; and
in a second state, the two clamp arms form a quadrilateral shape, wherein the first rod-shaped tube segments and the second rod-shaped tube segments of the two clamp arms form a majority of the quadrilateral shape.

2. The auricle clamp of claim 1, wherein the springs are U-shaped springs.

3. The auricle clamp of claim 2, wherein each U-shaped spring has two ends which are respectively inserted into holes at ends of the clamp arms, and the U-shaped spring and the clamp arm are combined together in an extrusion deformation, welding, adhesion or threaded connection manner.

4. The auricle clamp of claim 1, wherein the springs and the first and second rod-shaped tube segments are made of at least one of stainless steel, a cobalt-based alloy, a platinum-iridium alloy, a nickel-titanium alloy and a magnesium-based alloy.

5. The auricle clamp of claim 1, wherein the flexible lining wire is a nickel-titanium lining wire, and the nickel-titanium lining wire and the first rod-shaped tube segment and the second rod-shaped tube segment are fixed together by extrusion deformation.

6. The auricle clamp of claim 1, wherein outermost layers of the clamp arms and/or the springs are wrapped with a polyester vascular prosthesis or polyester braided fabric.

7. The auricle clamp of claim 1, wherein an outer sleeve is provided outside the clamp arms and the springs, and the outer sleeve is composed of a high molecular material.

8. A system, comprising:
   an auricle clamp sized for heart surgery, comprising:
   two clamp arms; and
   two springs located at two ends of the clamp arms respectively and are used for connecting the two ends of the two clamp arms to form a closed-loop structure and providing a clamping force enabling the two clamp arms to be located close to each other;
   wherein each of the two clamp arms comprises:
      a first rod-shaped tube segment and a second rod-shaped tube segment joined at a respective hinge site; and
      a flexible lining wire inserted into the first rod-shaped tube segment and the second rod-shaped tube segment such that the first rod-shaped tube segment and the second rod-shaped tube segment are pivotally connected; and
   wherein:
      in a first state, the two clamp arms are substantially parallel; and
      in a second state the two clamp arms form a quadrilateral shape wherein the first rod-shaped tube segments and the second rod-shaped tube segments of the two clamp arms form a majority of the quadrilateral shape; and
   a delivery device for conveying the auricle clamp to a root of the auricle in heart surgery, wherein the delivery device comprises:
      a handle;
      a coupler connected with the handle and capable of rotating relative to the handle;
      an outer tube connected with the coupler, wherein the outer tube rotates about a centre axis of the outer tube with the rotation of the coupler; a liner tube capable of moving within the
      outer tube along the centre axis of the outer tube;
      a trigger connected with the handle and capable of moving relative to the handle, wherein the trigger is connected to an end of the liner tube close to the handle so as to push the liner tube to move within the outer tube; and
      upper teeth and lower teeth for carrying the auricle clamp, pivotally connected to an end of the outer tube away from the handle, wherein the upper teeth and the lower teeth are connected to the liner tube respectively so as to pivot relative to the outer tube with movement of the liner tube within the outer tube to facilitate scissor-type opening and closing of the upper teeth and lower teeth.

9. The system of claim 8, wherein a chute is formed in the outer tube of the delivery device so that the liner tube can move along the chute.

* * * * *

UNITED STATES PATENT AND TRADEMARK OFFICE
CERTIFICATE OF CORRECTION

PATENT NO. : 10,905,433 B2
APPLICATION NO. : 15/744065
DATED : February 2, 2021
INVENTOR(S) : Qingliang Zhou et al.

Page 1 of 1

It is certified that error appears in the above-identified patent and that said Letters Patent is hereby corrected as shown below:

In the Claims

In Column 10, Line(s) 31, Claim 9, after "device", insert --,--.

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*